United States Patent [19]

Joa

[11] Patent Number: 4,576,600
[45] Date of Patent: Mar. 18, 1986

[54] FASTENERS FOR DIAPERS

[75] Inventor: Curt G. Joa, Ocean Ridge, Fla.

[73] Assignee: Curt G. Joa, Inc., Sheboygan Falls, Wis.

[21] Appl. No.: 713,336

[22] Filed: Mar. 18, 1985

[51] Int. Cl.⁴ .............................................. A61F 13/16
[52] U.S. Cl. .................................................... 604/390
[58] Field of Search ........................ 604/389, 390, 385

[56] References Cited

U.S. PATENT DOCUMENTS

| | | | |
|---|---|---|---|
| 4,127,132 | 11/1978 | Karami | 604/390 |
| 4,144,887 | 3/1979 | Milnamow | 604/390 |
| 4,178,933 | 12/1979 | Nemeth | 604/390 |
| 4,227,530 | 10/1980 | Schatz | 604/390 |
| 4,369,786 | 1/1983 | Miller | 604/390 |

Primary Examiner—John D. Yasko
Attorney, Agent, or Firm—Fuller, House, Hohenfeldt

[57] ABSTRACT

A diaper fastener strip has a first zone coated with a release material and a coat of adhesive over the release material and a second zone coated only with adhesive. The part of the strip having the second solely adhesive coated zone is adhered tenaciously to the margin of the fluid impermeable outer backing sheet of a diaper. The part of the strip having the first release material plus adhesive coated zone is folded over the diaper margin to contact the adhesive with the margin of the inner fluid permeable sheet of the diaper. When the strip is unfolded the adhesive transfers from the release material in the first zone to said inner sheet margin and becomes exposed for securing the diaper on a body. An alternative strip has said adhesive coated second zone adhered to the backing sheet and two consecutive zones next to it. The first zone most remote from the second zone may have adhesive coated over a release coating so when the first zone is folded over a third zone between the first and second zones and the strip is later peeled back, there will be adhesive transfer to an exposed in said third zone for securing the diaper on a body.

10 Claims, 3 Drawing Figures

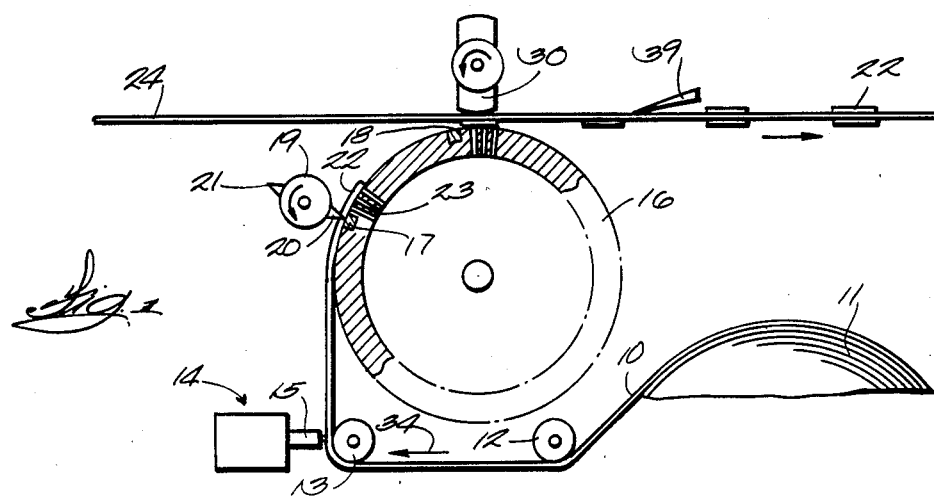
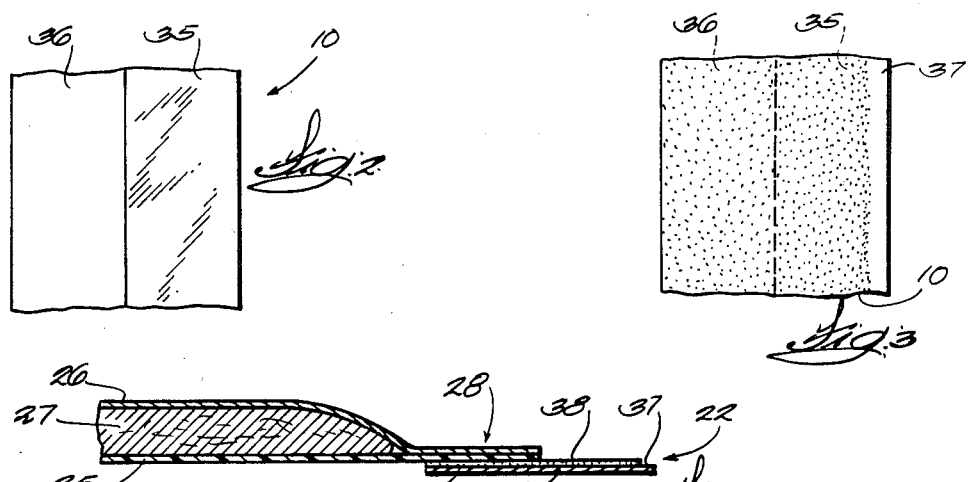
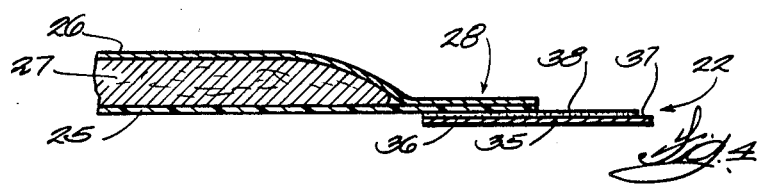
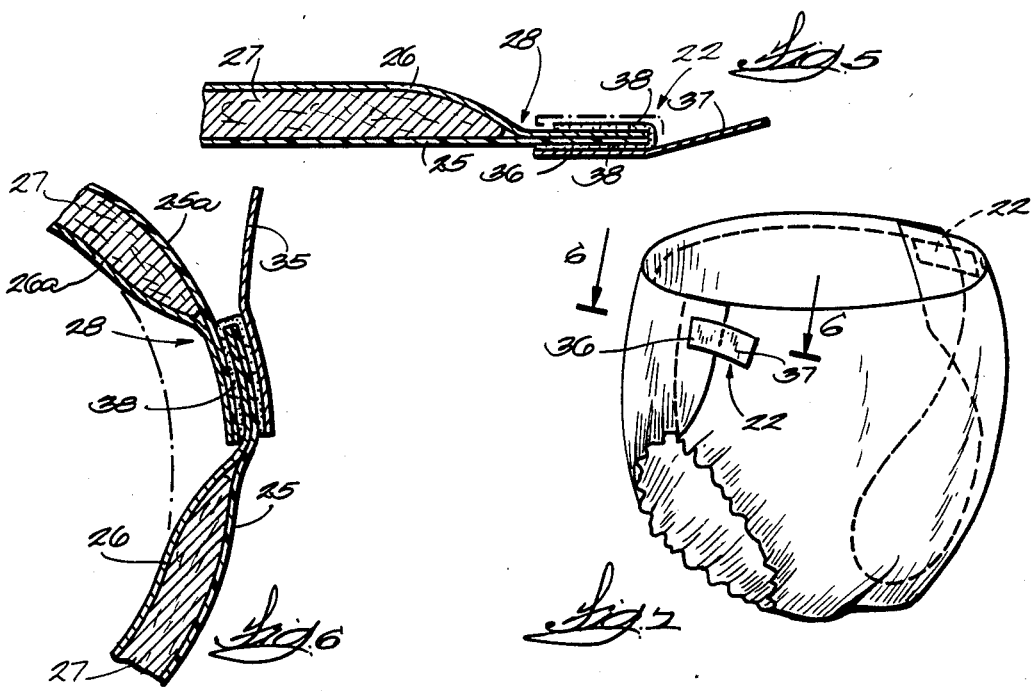

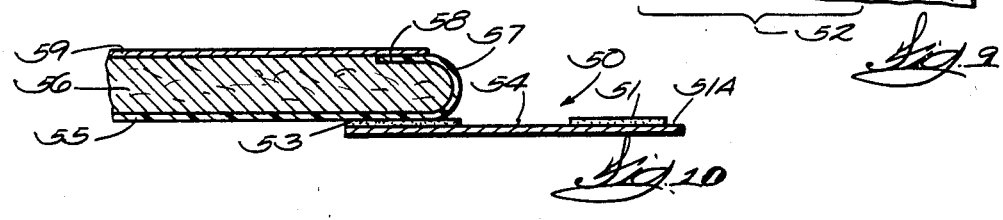
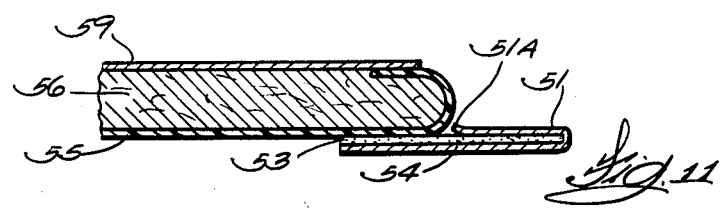
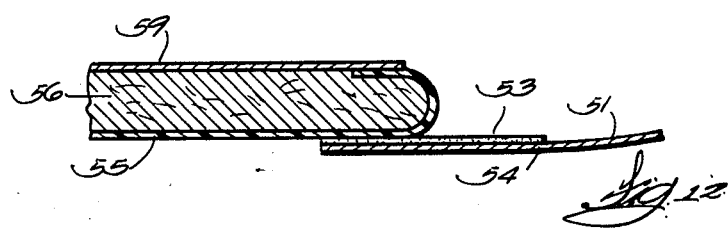
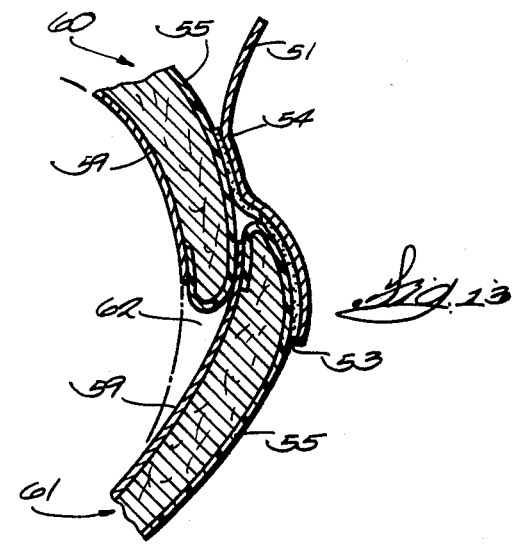

FASTENERS FOR DIAPERS

BACKGROUND OF THE INVENTION

This invention relates to improvements in disposable diaper fasteners of the type which use an adhesive bearing strip of tape to retain the diaper on a body such as that of an infant.

One objective of diaper machinery manufacturers is to provide for applying fasteners strips to a diaper web at high speed, using the least amount of material, and using the least complex and most reliable apparatus. Another objective is to provide fasteners that are easy to use and provide a secure attachment from one part of the diaper to another so the diaper will be retained snugly on the body.

Typically, the fastener strips are cut from a roll of paper tape or similar material which has one of its surface coated with a pressure sensitive adhesive. The strip from the roll is fed into the diaper making machine and cut into segments which are transferred by means of a vacuum roll to the moving diaper web. One end of the strip is pressed onto the margin of the diaper and the part of the strip which extends from the margin has a release strip superimposed on it so that said part can be folded over the release strip to thereby conceal the adhesive and prevent the strips from sticking to adjacent diapers after they are packaged. To use the fastener, the folded over part of the strip is peeled off of the release strip to expose the adhesive. The strip is then stretched across the edges of the diaper on the side of the body and pressed on the rear portion of the diaper to retain it on the body.

One of the problems that diaper machinery users have faced is that the available adhesives which are most commonly used to coat the one surface of the strip have poor shelf lives. The adhesive is especially susceptible to loss of its tackiness if it is stored for a considerable period of time in an ambient temperature environment that is above or not much lower than normal room temperature. Usually, special care is taken to prevent the rolls of adhesive coated tape from becoming too warm while they are in inventory.

Most prior art diaper fasteners are structurally complex and require many machine operations to fix them on the diaper web and to place them in a proper condition for packaging the diapers. Structural complexity usually means that a substantial amount of the strip, adhesive and release materials will be used in the fasteners. A fastener design that requires one more square centimeter of adhesive than another, for example, can result in a substantial increased cost factor in the diaper manufacturing business when one considers that a machine will make diapers typically at the rate of 350 or more per minute. In a 24 hour run of the machine, just requiring an additional drop of adhesive on each diaper can increase the amount of adhesive that must be purchased by a substantial amount. Loss of competitive position in the market place and lowering of profit in a diaper manufacturing business can be a consequence of using fasteners that consume any more than an optimal minimum amount of material in the manufacturing process.

SUMMARY OF THE INVENTION

The new fasteners disclosed herein have properties which permit fabricating them by a minimum number of operations, all on which are performed directly on the diaper making machine. The problem of degradation of the adhesive, even before the strips of the tape constituting the fasteners, are applied to the diapers is obviated.

The fasteners are adapted for use on disposable diapers which are formed as a continuous web in the diaper making machine. The web is ultimately cut into sections constituting the individual diapers. A fluid impermeable backing sheet, frequently of thin polyethylene, comprises the outer surface of the diaper web. A fluid permeable sheet, usually a nonwoven fibrous material, serves as the inner surface of the diaper which interfaces with the body when the diaper is applied. A pad of absorbent material is interposed between the outside backing sheet and the inside fluid permeable sheet and the sheets are usually substantially coextensive. The margin of the inner sheet is adhered to the margin of the outer sheet so there is protection against leakage to the edge of the diaper and so the absorbent material will be securely captured between the two sheets.

In accordance with one implementation of the new diaper fastener, one surface of a roll of tape, such as tough paper tape, from which the fasteners strips will be severed has one surface divided into two longitudinally extending contiguous zones. The first zone is coated with a release material such as silicone which has a weak affinity for adhesive. The adjacent zone is bare and has a strong affinity for adhesive. The tape is fed into the diaper making machine and at a first station both zones are coated with a pressure sensitive adhesive. This is followed by cutting a segment or strip from the tape and using a vacuum roll which interfaces with the uncoated surface of the strip to bring the first zone of the strip, having the strongly held adhesive, into secure adhesion with the margin of the backing sheet of the diaper web as it moves at high speed in a longitudinal direction. Next, the part of the strip that remains extending laterally from the web and that has the second release zone, which is also coated with adhesive, is folded over the edge of the diaper and made to stick on the margin of the inner fluid permeable sheet. Thus, no adhesive is exposed and, after the web is cut into individual diapers, they can be packaged without fasteners on one diaper sticking to fasteners on another diaper.

When the diaper is to be put in use, it is passed through the crotch of the body and one end is brought up over the front of the body and the other end is brought up over the rear of the body and the side edges are drawn toward each other so that the margin on the front can overlap the margin on the back sheet of the diaper. The diaper applier peels back the part of the adhesive coated strip that is undercoated with release material. The adhesive transfers and stays on the inner sheet of the diaper. The adhesive which has been transferred to the margin of the inside fluid permeable nonwoven sheet is then pressed against the outside of the outer impermeable plastic sheet to which the front of the diaper adheres tenaciously for securing the diaper on the body.

In another implementation of the fastener, especially suitable for rectangular diapers which are thick at their margins, the tape as acquired from the maker is coated with a release material over a longitudinally extending first zone that has a width of about ⅓ of the width of the tape. This leaves ⅔ of the width of the tape uncoated to provide a surface to which adhesive will adhere tenaciously. This tape is fed into the diaper making machine along the path of the moving diaper web. At a first station, pressure sensitive adhesive is applied to the narrow first zone that is coated with release material and a longitudinal stripe of pressure sensitive adhesive is concurrently applied over a second zone which is part of the zone on which there is no release material. This leaves a longitudinally extending central band or third zone on which there is no adhesive between the first zone that has the undercoat of release material and the second zone to which the adhesive has been applied directly to the tape. In this case, the part of the strip or second zone which is bare, that is, has no release material underlying it is pressed onto the outer backing sheet of the diaper web such that the laterally extending part of the fastener strip provides a central or third zone clear of adhesive next to the edge of the diaper while the release material undercoated first zone is most remote from the diaper edge. Thus, after the second zone of the strip is pressed onto the outer backing sheet of the diaper web, the strip is folded so that the first zone, coated with adhesive over release material, is placed in contact with the band or third zone on which no adhesive was applied. At the outer edge of the first zone no adhesive is applied to thereby provide a so called lift tab. When the diaper is to be placed in use, the folded part of the fastener strip is gripped at the left tab and peeled back and unfolded in which case the adhesive from the first zone transfers to the central uncoated third zone of the fastener strip to which the adhesive adheres strongly. This leaves the first zone on the strip coated with the release material and unsticky. This unsticky portion of the fastener strip can be gripped to pull part of the diaper that covers the front of the body toward the part that covers the rear of the body so that the part of the strip with the exposed adhesive can be pressed against the outside of the outer fluid impermeable backing sheet to which the strip adheres tenaciously for securing the diaper to the body.

How the concept of effecting transfer of adhesive from a zone on a fastener strip to another zone on the strip or to a surface of the diaper is implemented will appear in the ensuing more detailed description of embodiments of the invention which will now be set forth in reference to the drawings.

DESCRIPTION OF THE DRAWINGS

FIG. 1 is a schematic diagram of those parts of a diaper making machine which are involved in the fabrication of the diaper fasteners and their application to a diaper web;

FIG. 2 is a sample of a tape which has a first zone extending across part of its width coated with a release material adjacent a second zone of bare tape;

FIG. 3 shows the entire surface of the tape coated with an adhesive material;

FIG. 4 shows the margin of a diaper web to which a segment or fastener strip cut from of the tape in FIG. 3 has been applied wherein one end of the strip is adhered to the backing sheet of the diaper and the remainder, particularly the zone having adhesive over release material still extends laterally away from the margin of the diaper;

FIG. 5 is a fragmentary vertical cross section of the diaper web wherein the zone of the fastener strip having adhesive overlaying release material has been folded over the inner surface of the margin of the diaper as indicated by dash dot lines and then unfolded to cause transfer of the adhesive to the diaper so as to leave a strip end that is not coated with adhesive;

FIG. 6 is a partial section taken along line 6—6 in FIG. 7 showing how the front of the diaper is joined with the rear of the diaper with the fastener shown in FIGS. 2-5;

FIG. 7 is a perspective view of a diaper in the form it takes when it is fixed to the body with the new fasteners;

FIG. 8 shows a tape used in a second implementation of the invention which tape has a release zone covering about one-third of the tape width and the larger remainder of the width of the tape being bare;

FIG. 9 shows the tape with a stripe of adhesive deposited on part of the width of the one zone and another strip of adhesive deposited over the release zone to thereby leave a bare zone of the strip between said zones;

FIG. 10 shows the fastener strip cut from the tape and attached to the margin of a typical rectangular diaper where one end of the fastener strip is tenaciously adhered to the backing sheet of the diaper and there is another laterally extending free end on which there is a coating of adhesive over the release material;

FIG. 11 shows the adhesive and release material coated free end of the fastener strip folded over its bare central zone as is the case when the diapers are stored in packages;

FIG. 12 shows the portion of the fastener strip having the adhesive over the release material coating unfolded to cause the adhesive that originally coated said portion to transfer to the central zone of the fastener strip; and FIG. 13 shows a fragment of the front and rear parts of a diaper fastened together with the fastener means depicted in FIGS. 8-12.

DESCRIPTION OF A PREFERRED EMBODIMENT

FIG. 1 is a diagram of a suitable machine for forming the improved diaper fasteners and for attaching them to a diaper web at constant intervals along the web. A more detailed showing of the significant features of this fastener strip applying apparatus may be seen in U.S. Pat. No. 4,171,239 which is owned by the assignee of this application.

In FIG. 1, the tape 10 that is used for making the fastener strips is fed from a parent roll 11 over guide rollers 12 and 13 to proximity with a hot melt pressure sensitive adhesive applicator 14. The applicator has a nozzle 15 which deposits a coating of adhesive on one or more longitudinally extending zones on the tape. The tape then passes onto a large diameter roll 16 whose interior may be coupled to a vacuum source, not shown. Thus, the interior of the roll 16 may be considered to be at a negative pressure relative to the atmosphere. A plurality of cutter anvils such as those marked 17 and 18 are embedded in the periphery of vacuum roll 16. These anvils rotate past a power driven cutter wheel 19 that has radially extending radial blades 20 and 21 which periodically rotate into alignment with an anvil, such as the one marked 17, to thereby cut off an adhesive coated segment or diaper fastener strip 22 from tape 10. A plurality of radial holes 23 let the vacuum in roll 16 be applied to the face of fastener strip 22 on which there is no adhesive so that the strips 22 can be carried on roll 16 by vacuum to alignment with a rotary pressing device 30 where the strips are pressed onto the margin of a diaper web 24. Adhesion of the fastener strips 22 to the diaper web 24 is strong enough to overcome the vacuum force in which case the fastener strips are freed from the roll 16 and are carried along the diaper web in longitudinally spaced apart relationship.

A fragmentary vertical section of one type of diaper with which the new fastener may be used is shown in FIG. 4. One may assume that this diaper has been segregated from continuous diaper web 24 in FIG. 1 after the fastener strips 22 have been applied to opposite side margins of the diaper. The diaper in FIG. 4 is comprised of an outer or backing sheet 25 which, in most diapers, is a thin sheet of moisture impermeable plastic such as polyethylene. The backing sheet 25 faces away from the body when the diaper is applied in the crotch region. The inside sheet, that is, the sheet that interfaces with the surface of the body, is comprised of a moisture permeable sheet 26 of nonwoven material. A wad of absorbent material 27 is captured between impermeable backing sheet 25 and the nonwoven body interfacing sheet 26. Typically, a continuous backing sheet 25 is conveyed through the diaper making machine with wads of absorbent material 27 regularly spaced apart from each other on the sheet. One or more stripes of adhesive are applied continuously to the margin of backing sheet 25 so that when the inner sheet 26 is fed in, its margin will be adhered to the margin of the backing sheet to form a flexible flange or flap which extends all of the way around the diaper perimeter and is indicated by the numeral 28. One embodiment of the new fastener is indicated generally by the numeral 22 in FIG. 4.

The manner in which said one embodiment of the new fastener is fabricated and used will now be described. A fragment of the tape 10 unreeled from roll 11 in FIG. 1 is shown in FIG. 2. This fragment shows that the tape taken from roll 11 has two longitudinally extending bands or zones 35 and 36. The first zone 35 extends over about ½ of the width of the tape 10 and is coated with a release material such as silicone. Tape 10 is typically composed of tough paper. The silicone coating on first zone 35 adheres tenaciously to the paper substrate but it is glossy and slippery after it is cured so that adhesive will not adhere to it. The other or second zone 36, about one-half of the tape width is simply uncoated or bare paper.

Referring to FIG. 1, tape 10 is fed in the direction of the arrow 34 over guide rollers 12 and 13 to an adhesive applicator 14 which has a nozzle 15 that in this case coats the full width of tape 10 with a pressure sensitive adhesive. The stippling on tape 10 in FIG. 3 is indicative of it having been coated over most of its width with adhesive except for a narrow band 37 at its end which band consitutes a lift tab. The tape proceeds from the glue applicator in FIG. 1 to rotary cutter 19 where one or the other of the blades 20 or 21 comes into contact with an anvil 17 on vacuum roll 16 to thereby cut off a segment or strip 22 of the tape. At this time the face of the strip that is not coated with adhesive is interfaced with roll 16 in alignment with holes 23 through which vacuum is applied to the strip 22 for holding it as it is carried along roll 16 toward press roll 23 where the second zone 36 at one end of the fastener strip which has an adhesive coat but no underlying release coat is pressed onto the side flap 28 of the diaper web 24. The peripheral speed of vacuum roll 16 is low compared to the lineal speed of diaper web 24 so that the fastener strips 22 are spaced along each edge of the web 24. Attachment of the fastener strip 22 to the flap 28 of the diaper is shown in FIG. 4 where the adhesive coating is shown in exaggerated thickness and given the reference numeral 38. The second zone 36, wherein the bare tape was coated with adhesive only, adheres tenaciously to impermeable diaper backing sheet 25. In FIG. 4, the zone 35 which has adhesive 38 applied over release material is presently extending laterally from the diaper web as it would be after the strip 22 passes the press roll 30 in FIG. 1. After passing the press roll, the strips 22 encounter a conventional folding device 39. This device is somewhat like a plow and turns the laterally extending end of the fastener strip 22 over the edge of diaper flap 28 so as to cause the adhesive on the release material coated first zone 37 to be brought into contact with the inner nonwoven material sheet 26 on the flap 28 of the diaper web. The individual diapers can now be severed from the web and packaged.

In FIG. 5, the diaper has been made ready for attaching it to a body such as that of an infant. In FIG. 5, the release material coated first zone 35 of strip 22 has been peeled off of the nonwoven material 26 on the top of flap 28 by gripping the unadhered release coated lift tab 37 of the strip. When the free end containing first zone 35 was folded over to interface with the nonwoven face of the diaper flap 28, this zone was at the position indicated by the dash-dot lines in FIG. 5. Because the release material coated first zone 35 has a weak affinity for the adhesive, as can be seen in FIG. 5, the adhesive 38 is transferred from zone 35 to the nonwoven sheet 26 on the inner side of the diaper. The free end of the strip containing release material coated zone 35 is now free of any tacky material and can be used by the person applying the diaper to the body to stretch that part of the diaper which is in front of the body when it is passed through the crotch to overlap the margin of the diaper portion that is extending around the back of the body. This permits the attachment of the fastener to be made at the side of the body.

In FIG. 6, the thickness of sheets 25 and 26 and the thickness of adhesive layer 38 are shown with exaggerated thicknesses. The outer fluid impermeable backing sheet of the diaper coming around the back of the body is marked 25a and the inner sheet is marked 26a. The portion of the backing sheet 25 coming around the front of the body to its side is marked 25 again and the inner sheet is marked 26. The lead line from the reference numeral 38 indicates where the adhesive layer that has been transferred to the nonwoven material 26 in the area of the diaper flap 28 interfaces with that part of the flap having the backing sheet 25a margin. Since the adhesive 38 is strongly bonded in inner nonwoven sheet 26 and since the backing sheet 25a in the flap or margin of the diaper has a strong affinity for the adhesive, the overlapped front and rear margins on the diaper become strongly joined to each other. As shown in FIG. 6, the free end zone 35 of the fastener strip extends outwardly without any adhesive on it and its opposite end remains bonded to the outer backing sheet 25. FIG. 7 shows how the front edge and back edge of the diaper overlap so that the adhesive which has been transferred from the tape strip 22 to the inner nonwoven material sheet 26 along the diaper flap 28 can be pressed onto the backing sheet to effect adhesion.

FIGS. 8–13 show another implementation of a fastener that is based on the adhesive transferring concept. Here the original tape is designated by the reference numeral 50 and is fed into the diaper making machine from a roll such as roll 11 in FIG. 1. Tape 50 may be comprised of tough paper, for example. As shown in FIG. 8, the parent tape has a longitudinally extending first zone, 51 equal to about ⅓ of its width coated with a release material. A zone 52 equal to about another ⅔ of the width of the tape 50 is bare. As the tape passes through applicator nozzle 15, two stripes of adhesive are applied, thereby dividing the tape into first, second and third zones 51, 54, 53 across its width. First zone 51, which has been coated with a release material such as silicone, now has a coating of pressure sensitive adhesive applied to it except for a narrow band 51A near its edge which serves as a lift tab. As mentioned earlier, the release material coat has a low affinity for the adhesive. Third zone 53 also has a band of adhesive applied directly to the bare strip by nozzle 15. In this example, adhesive coated third zone 53 is about ⅓ of the width of tape 50. The bare paper underlying third adhesive coated second zone 53 has a strong affinity for the adhesive. The central or third zone 54 in FIG. 9 remains bare, that is, in this zone, neither release material nor adhesive is applied. The tape, in the condition depicted in FIG. 9, is fed past the cutter 19, as in FIG. 1 where fastener strips or segments are cut from the tape. As in the previously discussed embodiment, these strips are held on the periphery of roll 16 by the several vacuum ports 23 until reaching the press roll 30 where second zone 53 of the fastener strip, which is coated with adhesive only, is pressed onto the impermeable backing sheet 55 comprising the diaper web. Zone 53 adheres tenaciously to the margin of impermeable backing sheet 55.

In this case the diapers cut from the web are of the type having a rectangular shape. A fragmentary vertical section through such a diaper is depicted in FIG. 10. It is comprised of a fluid impermeable backing sheet 55 on which there is a layer of fluid absorbent material 56 such as cellulose fluff. The margin of the backing sheet 55 is folded around as at 57 to form a reentrant flange or margin 58. As is typical, before the first zone 53 of the fastener tape is pressed onto the diaper web margin, narrow glue stripes are applied continuously to backing flange 58 and a fluid permeable nonwoven sheet 59 is then laid onto the flange 58 to secure the margin of the inner nonwoven sheet 59 to the margin of the impermeable outer sheet 55.

FIG. 10 shows the fastener strip cut from tape 50 fastened to the margin of the diaper web. The adhesive layer in the second zone 53 has its thickness exaggerated in FIG. 10 to make it evident that the adhesive tightly bonds the fastener strip 50 to the backing sheet 55. This leaves bare second or mid-zone 54 and adjacent adhesive coated and release material undercoated first zone 51 extending laterally from the diaper web. After the second zone 53 of the fastener strip is pressed on the diaper web as in FIG. 10, it reaches a folding device such as the plow 39 in FIG. 1 which folds the adhesive coated and release material undercoated first zone 51 over the bare third zone 54 in the mid-region of the strip to put the fastener strip in condition for storage as depicted in FIG. 11.

In FIG. 11, one may see that the adhesive and release material coated zone 51 has now been interfaced with the formerly bare central third zone 54 of the strip. Since the formerly bare central zone 54 has a strong affinity for the adhesive, the adhesive on undercoated zone 51 adheres preferentially to the tape strip and weakly to the release material coated width of the strip. After the fasteners are folded as in FIG. 11, the diaper web is cut into individual diapers which are then packaged. When the diaper is to be applied to the body of an infant, the fingers are used to grip the release material coated lift tab 51A of the strip which is clear of adhesive and the strip is unfolded as in FIG. 12. Because of the undercoating of release material on the first zone 51, the adhesive is released from zone 51 and becomes deposited on the originally bare third zone 54 which is not coated with release material. Thus, the adhesive adheres tenaciously to central or third zone 54 of the strip and the adhesive becomes exposed. The free end having zone 51 can be peeled back as the ast step after the diaper has been passed through the crotch of the infant to avoid inadvertent adherence of the fastener strip to some part of the diaper to which it should not be adhered.

When the diaper is applied through the crotch of the body, one end is pulled up along the front of the body and the other end is pulled up over the rear. The side margins of the diaper are caused to overlap at this time as depicted in FIG. 13. Here the part of the diaper that extends around the back of the infant is marked 60 and the part that extends around the front of the infant is marked 61. The side of the infants body is represented by the dashed line marked 62. Thus, in FIG. 13, the moisture impermeable backing sheet 55 of the diaper is presented outwardly. Now the adhesive in central third zone 54 which has been transferred from release material coated first zone 51 is pressed onto the backing sheet 55 to effect a tenacious bond for securing the diaper on the infant. Of course, as indicated in FIG. 7, fasteners are applied to both side margins of the diaper web in the machine of FIG. 1 so that both sides of the diaper can be closed snugly when applied to the infant.

I claim:

1. A fastener for a disposable diaper, the diaper comprising a fluid permeable inside sheet for interfacing with the body, a moisture-impermeable outer backing sheet substantially coextensive with the inner sheet and bonded about its margins to said inner sheet, and absorbent material interposed between said inner and outer sheets, said fastener comprising:

a strip of tape having an inner surface and an outer surface, said inner surface having a first zone constituting a release zone that has a low affinity for an adhesive and a second zone that has a high affinity for said adhesive adjacent said first zone, a coat of adhesive on said inner surface of said strip over said first release zone and over said second zone, the part of said strip containing said second zone being adhered tenaciously to said impermeable outer backing sheet of the diaper at the margin of the diaper and the part of said strip containing said first release zone being folded around the edge of said diaper to place the adhesive coated release zone of the inner surface of said strip in contact with the margin of said inside fluid permeable sheet of the diaper to conceal the adhesive for facilitating storage of the diaper, peeling the part of said fastener strip having the release zone from said inside sheet causing said adhesive to transfer from said release zone of the fastener strip to the margin of said inside sheet so the resulting adhesive coated area on said inside sheet may be pressed onto said outer sheet remotely from said area to secure the diaper on a body.

2. The fastener according to claim 1 wherein the widths of said first release zone and said second zone are about one-half the width of said tape.

3. The fastener according to claim 1 wherein said adhesive is applied over the entire width of said second zone having a high affinity for the adhesive and is applied over most of the width of said release zone to leave a stripe at the margin of said release zone uncoated with adhesive and serving as a lift tab for being gripped to peel said strip.

4. A fastener for a disposable diaper of the type comprised of a fluid impermeable outer backing sheet and a fluid permeable inner sheet, said sheets being bonded to each other along their margins, and a fluid absorbent material disposed between said sheets, said fastener comprising:
  a strip comprised of a material having a high affinity for a pressure sensitive adhesive, said strip having one of its surfaces divided into first and second adjacent zones,
  a release material coating on the first of said zones having a low affinity for adhesive and a layer of pressure sensitive adhesive overlaying said release material coating and also overlaying the second of said zones having said high affinity for adhesive,
  the part of said strip having said second zone being adhered to said backing sheet at the margin of the diaper and the part of said strip having said first zone being folded around the margin of said diaper to put the adhesive on said release material coated first zone in contact with said inner sheet, such that when said part of said strip having said release material is peeled off said adhesive is transferred to said inner sheet and exposed for being pressed on to said backing sheet to secure the diaper on a body.

5. The fastener according to claim 4 wherein said release material is silicone.

6. The fastener according to claim 4 wherein adhesive is omitted from a stripe at an end of said strip in the zone coated having release material coating to provide a lift tab that is unadhered to said inner sheet to facilitate peeling of said strip.

7. A fastener for a disposable diaper of the type comprised of a fluid impermeable outer backing sheet and a fluid permeable inner sheet for interfacing with a body, said sheets being bonded to each other along their margins, and a fluid absorbent material disposed between said sheets, said fastener comprising:
  a strip comprised of a material having a high affinity for a pressure sensitive adhesive, one surface of said strip having a first zone at one end of the strip coated with a release material that has low affinity for adhesive, said release material being coated with adhesive, a second zone at the other end of said strip coated with adhesive and a third zone between said first and second zones,
  the part of said strip having said second zone being adhered to said margin of the backing sheet and the part of said strip having said first zone being folded over said third zone to place the adhesive on the first zone in contact with said third zone such that when said part having the first zone is peeled off and unfolded said adhesive transfers from said first zone to said third zone and is exposed for being pressed on said backing sheet to secure the diaper on a body.

8. The fastener according to claim 7 wherein said zones have substantially equal widths.

9. The fastener according to claim 7 wherein the width of each of said zones is about equal to one-third of the width of the strip.

10. The fastener according to claim 7 wherein there is a stripe at said one end of said strip having the release material coated first zone which stripe is uncoated with adhesive to provide a lift tab for being gripped to peel said strip.

* * * * *